(12) United States Patent
Suzuki et al.

(10) Patent No.: US 7,674,734 B2
(45) Date of Patent: *Mar. 9, 2010

(54) POLYPROPYLENE NONWOVEN FABRIC AND USE THEREOF

(75) Inventors: Kenichi Suzuki, Ichihara (JP); Akio Matsubara, Ichihara (JP); Shigeyuki Motomura, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/181,937

(22) Filed: Jul. 29, 2008

(65) Prior Publication Data

US 2008/0287027 A1 Nov. 20, 2008

Related U.S. Application Data

(62) Division of application No. 11/720,203, filed on May 25, 2007, now Pat. No. 7,585,796.

(51) Int. Cl.
*D04H 3/16* (2006.01)
*D04H 3/00* (2006.01)
*C08L 23/00* (2006.01)
*A61F 13/15* (2006.01)

(52) U.S. Cl. .................. 442/401; 442/361; 525/240; 604/358

(58) Field of Classification Search .......... 442/401, 442/361
See application file for complete search history.

(56) References Cited

FOREIGN PATENT DOCUMENTS

| | | | |
|---|---|---|---|
| JP | 08-049166 | 2/1996 | |
| JP | 2004-238775 | * | 8/2004 |
| TW | 200304510 A | 10/2003 | |
| WO | 9315251 | 8/1993 | |
| WO | 0194462 | 12/2001 | |
| WO | 02065679 | 8/2002 | |
| WO | 03040201 | 5/2003 | |

OTHER PUBLICATIONS

International Search Report for PCT/JP2005/021738 dated Feb. 21, 2006.
Taiwanese Office Action dated Sep. 6, 2007 corresponding to U.S. Appl. No. 11/720,203, filed May 25, 2006.

* cited by examiner

*Primary Examiner*—Lynda Salvatore
(74) *Attorney, Agent, or Firm*—Turocy & Watson, LLP

(57) ABSTRACT

A polypropylene based nonwoven fabric is excellent in surface appearance and stretch properties and exhibits a small residual strain and excellent adhesiveness to polyolefins. The nonwoven fabric is obtained by forming a polypropylene resin composition comprising 1 to 40 weight parts of (i) an isotactic polypropylene, and 60 to 99 weight parts of (ii) a propylene/ethylene/α-olefin copolymer obtained by copolymerizing 45 to 89 mole % of propylene, 10 to 25 mole % of ethylene and the balance of α-olefin having 4 to 20 carbon atoms (with the proviso that the copolymerized amount of the α-olefin having 4 to 20 carbon atoms does not exceed 30 mole %), characterized by a small residual strain after stretching at a stretch ratio of 150%. The nonwoven fabric can be effectively used as sanitary materials or the like by virtue of its characteristics including stretch properties.

24 Claims, 2 Drawing Sheets

POLYPROPYLENE NONWOVEN FABRIC AND USE THEREOF

CROSS-REFERENCE TO RELATED APPLICATIONS

This application is based upon and claims the benefit of priority from the prior Japanese Patent Application No. 2004-343200, filed on Nov. 26, 2004, the entire contents of which are incorporated herein by reference.

This application is based upon and claims the benefit of priority from the prior PCT Application No. PCT/JP2005/021738, filed on Nov 25, 2005, the entire contents of which are incorporated herein by reference.

This application claims the benefit of and is a Divisional application of U.S. patent application Ser. No. 11/720,203 filed on May 25, 2007, now U.S. Pat. No. 7,585,796 the entire contents of which are incorporated herein by reference.

TECHNICAL FIELD

The present invention relates to a nonwoven fabric which is excellent in stretch properties and exhibits a small residual strain and excellent in sense of touch, and its use. More particularly, the invention relates to a nonwoven fabric having excellent properties which is obtained by forming a specific polypropylene composition and its use.

BACKGROUND ART

Polypropylene is cheap, excellent in rigidity, humidity resistance and heat resistance, and also superior in moldability. So, using these properties, nonwoven fabrics have been produced in large quantities and begun to be used for various applications including sanitary materials.

However, propylene has properties such that the rigidity is high but stretch properties are not sufficient so that it has been considered that a nonwoven fabric composed of polypropylene could not be used in the field requiring stretch properties and a small residual stain. When such stretch properties are required, thermoplastic polyurethane has hitherto been used in many cases (Patent Document 1).

By using a soft polyolefin instead of polyurethane (Patent Document 2), a prescribed improvement has been exhibited but there have been problems such that surface appearance of a mold product is poor and sense of touch is also poor for the applications requiring stretch properties as described above.

Furthermore, a soft polyolefin and an isotactic polypropylene are continuously polymerized (Patent Document 3) to be used for an elastic fiber in some cases, whereas the mixture ratio of the soft polyolefin and isotactic polypropylene, and an effect on stretch properties are not clearly shown.

Further, when a blend composition of the soft polyolefin and low viscosity homopolypropylene with high MFR (250 to 550) are processed into a fiber or the like, processability and flexibility (drape property) are obtained (Patent Document 4). However, there is no description of stretch properties.

On the other hand, when a copolymer having a component unit composed of styrene is used, stretch properties are excellent, but rigidity is not sufficiently exhibited and adhesiveness to a nonwoven fabric composed of polyolefin or a film composed of polyolefin is bad. Thus, when it is used as a sanitary material or the like, a problem in adhesion might be an obstacle, causing a problem in that it is not possible to freely design products.

Patent Document 1: WO 2002/65679 pamphlet
Patent Document 2: WO 1993/15251 pamphlet
Patent Document 3: WO 2003/040201 pamphlet
Patent Document 4: WO 2001/094462 pamphlet

DISCLOSURE OF THE INVENTION

Problem to be Solved by the Invention

An object of the present invention is to provide a novel nonwoven fabric using polypropylene and a propylene/ethylene/α-olefin copolymer and its use.

Furthermore, another object of the present invention is to provide a polyolefin based nonwoven fabric which is excellent in surface appearance and stretch properties, exhibits a small residual strain and is excellent in adhesiveness to polyolefins, and its use.

Means to Solve the Problem

The nonwoven fabric of the present invention is a nonwoven fabric obtained by forming a polypropylene resin composition comprising
  (i) 1 to 40 weight parts of an isotactic polypropylene, and
  (ii) 60 to 99 weight parts of a propylene/ethylene/α-olefin copolymer obtained by copolymerizing 45 to 89 mole % of propylene, 10 to 25 mole % of ethylene and the balance of α-olefin having 4 to 20 carbon atoms, with the proviso that the copolymerized amount of α-olefin having 4 to 20 carbon atoms does not exceed 30 mole %.

It is preferable that the nonwoven fabric of the present invention has a residual strain of less than 50% after stretching at a stretch ratio of 150% of the nonwoven fabric.

Furthermore, the nonwoven fabric of the present invention can be used as a sanitary material, a disposable diaper, a sanitary material, an absorbent article, a disposable face mask, an adhesive plaster, a patch, a disposable surgeon gown, a rescue gown, various medical films or sheets.

The nonwoven fabric of the present invention is formed by using a fiber obtained using (i) an isotactic polypropylene and (ii) a propylene/ethylene/α-olefin copolymer obtained by copolymerizing propylene, ethylene and as needed other α-olefins in a prescribed amount so that it can be used as a nonwoven fabric having a stretchability, exhibiting a small residual strain after stretching at a stretch ratio of 150% and having elasticity. Further, since filaments are hardly broken in a spinning step during the production of the nonwoven fabric of the present invention, it is possible to produce the nonwoven fabric of the present invention with good efficiency.

EFFECT OF THE INVENTION

The nonwoven fabric of the present invention is a stretchable nonwoven fabric which is excellent in surface appearance and stretch properties, and exhibits a small residual strain. Besides, the nonwoven fabric of the present invention can be adhered very well even with a polyolefin based adhesive when a predetermined shape is given by using a nonwoven fabric, different from a polyurethane based nonwoven fabric.

BEST MODE FOR CARRYING OUT THE INVENTION

Figure 1:
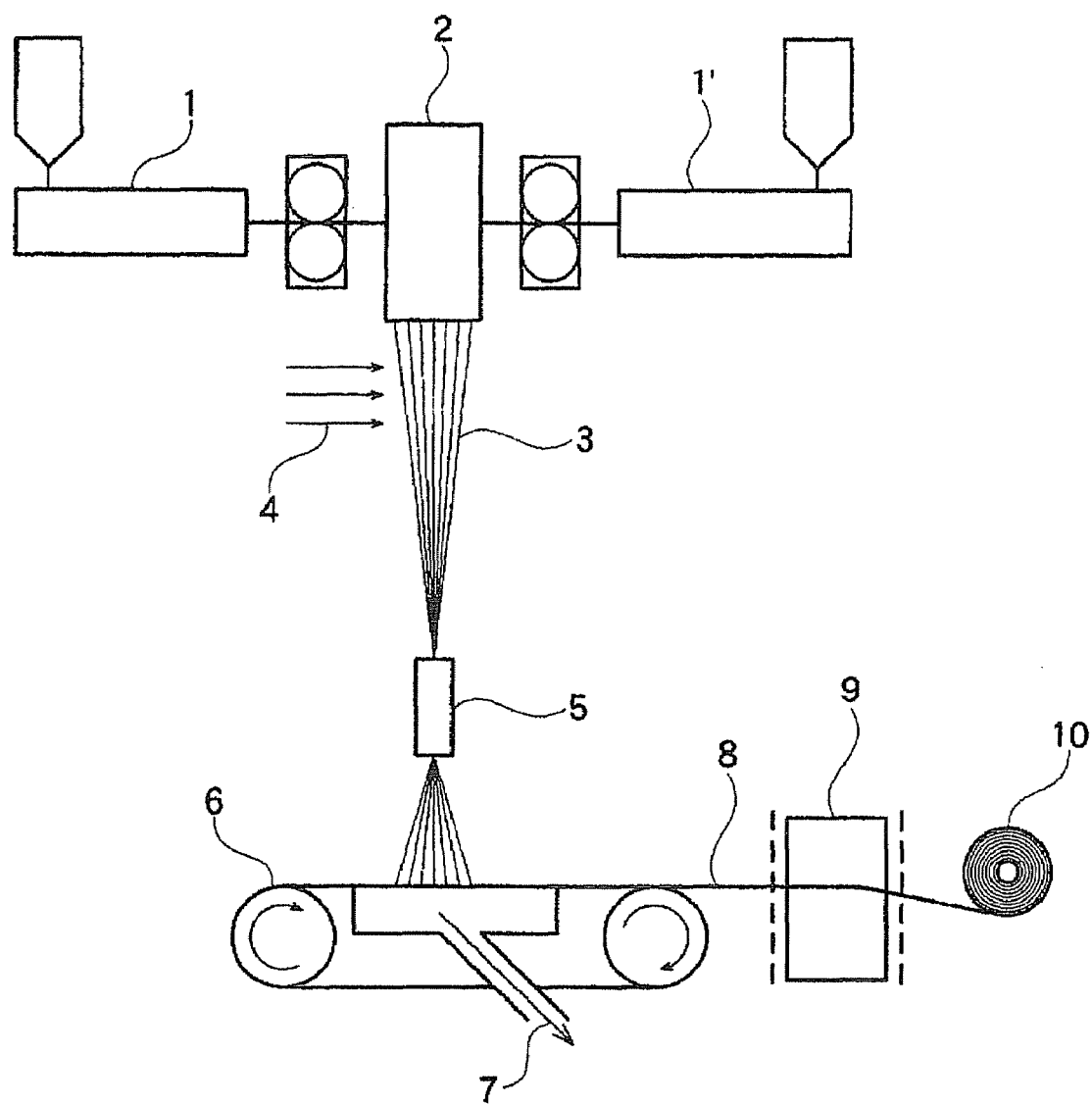
FIG. 1 is a schematic view illustrating an embodiment of a nonwoven fabric manufacturing machine used in Examples 11 to 13.

The nonwoven fabric of the present invention and its use will be described in more detail below.

The nonwoven fabric of the present invention is a nonwoven fabric formed from a fiber obtained by spinning using a resin composition formed from a propylene based polymer comprising (i) an isotactic polypropylene and (ii) a propylene/ethylene/α-olefin copolymer obtained by copolymerizing propylene, ethylene and as needed other α-olefins in a prescribed amount.

The propylene based polymer composition constituting the nonwoven fabric of the present invention will be described in more detail below.

A resin for a fiber forming the nonwoven fabric of the present invention is formed from an olefin based composition comprising (i) an isotactic polypropylene and (ii) a propylene/ethylene/α-olefin copolymer obtained by copolymerizing propylene, ethylene, and as needed α-olefin in a specific amount.

First, each component of (i) and (ii) contained in the propylene based polymer composition will be explained.

(i) Isotactic Polypropylene

In the present invention, in order to form a propylene based resin composition for the production of a nonwoven fabric, a specific propylene polymer having specific characteristics is used. Polypropylene used in the present invention may be a homopolypropylene, a propylene/α-olefin random copolymer or a propylene block copolymer as far as they have the following characteristics. However, polypropylene is preferably a homopolypropylene or a propylene/α-olefin random copolymer.

A melt flow rate (MFR; ASTM D1238, at 230° C. under a load of 2.16 kg) of (i) the isotactic polypropylene used in the present invention is not particularly limited as far as MFR after giving a composition is preferable for the formation of a nonwoven fabric. But, it is usually from 0.1 to 2000 g/10 minutes, preferably not less than 1 g/10 minutes but less than 250 g/10 minutes, and further preferably from 0.1 to 100 g/10 minutes. Further, a melting point of the isotactic polypropylene to be determined by the DSC measurement is usually not less than 120° C., preferably not less than 130° C., and further preferably not less than 150° C.

When (i) the isotactic polypropylene used in the present invention is a propylene/α-olefin random copolymer, α-olefin is preferably selected from ethylene and/or α-olefin having 4 to 20 carbon atoms. Such α-olefin is contained usually in the amount of from 0.3 to 7 mole %, preferably from 0.3 to 6 mole % and further preferably from 0.3 to 5 mole %.

The isotactic polypropylene (i) used in the present invention can be produced by various methods. Its production methods are not particularly limited. For example, the isotactic polypropylene produced by polymerizing in the presence of a polymerization catalyst such as a Ziegler Natta catalyst, a metallocene catalyst or the like can be easily available from the market and such a commercial isotactic polypropylene can be used as it is.

(ii) Propylene/ethylene/α-olefin Random Copolymer The propylene/ethylene/α-olefin random copolymer (ii) used in the present invention is required to be obtained by copolymerizing a propylene component in the range of 45 to 89 mole %, an ethylene component in the range of 10 to 25 mole % and an α-olefin component having 4 to 20 carbon atoms in the range of 0 to 30 mole %. (ii) The propylene/ethylene/α-olefin random copolymer obtained by copolymerizing a propylene component, an ethylene component and an α-olefin component in such amounts is used, whereby it is possible to obtain an olefin based composition which has stretch properties, exhibits a small residual strain and can be easily spun, together with (i) the isotactic polypropylene.

In particular, the copolymerized amount of the propylene component in (ii) the propylene/ethylene/α-olefin random copolymer used in the present invention is preferably from 45 to 80 mole % and particularly preferably from 50 to 75 mole %. The copolymerized amount of the ethylene component is preferably from 10 to 23 mole % and particularly preferably from 12 to 23 mole %. Further, the α-olefin component having 4 to 20 carbon atoms to be copolymerized as needed in (ii) the propylene/ethylene/α-olefin random copolymer is preferably contained within the range of 0 to 25 mole % and particularly preferably in the range of 0 to 20 mole %.

In (ii) the propylene/ethylene/α-olefin random copolymer obtained by copolymerizing a propylene component, an ethylene component and an α-olefin component having 4 to 20 carbon atoms in such amounts, its compatibility with the isotactic polypropylene becomes good. A nonwoven fabric in a preferred embodiment as described above can be produced from the propylene based polymer composition obtained by forming it into a composition.

In (ii) the above propylene/ethylene/α-olefin random copolymer to be used in the present invention, an intrinsic viscosity [η] measured in decalin at 135° C. is usually in the range of 0.01 to 10 dl/g and preferably in the range of 0.05 to 10 dl/g. When the intrinsic viscosity [η] of (ii) the propylene/ethylene/α-olefin random copolymer is within the above range, it is mixed with the isotactic polypropylene to prepare an olefin based composition, both of them can be uniformly kneaded. So, the nonwoven fabric obtained by spinning this olefin based composition is also highly uniform, thus having good characteristics.

Of the aforementioned propylene/ethylene/α-olefin copolymer (ii), in the present invention, it is preferred to use a copolymer in which a stress at 100% strain (M100) measured at 23° C. at a distance between spuns of 30 mm with a tensile speed of 30 mm/minute by using a JIS No. 3 dumbbell in accordance with JIS K6301 is usually not more than 4 Mpa, preferably not more than 3 Mpa and further preferably not more than 2 Mpa.

Furthermore, (ii) the propylene/ethylene/α-olefin random copolymer having the degree of crystallinity measured by X-ray diffraction of not more than 20% and preferably from 0 to 15% can be preferably used. Further, (ii) the propylene/ethylene/α-olefin random copolymer has a single glass transition temperature and such a glass transition temperature (Tg) measured by a differential scanning calorimeter (DSC) is demanded to be usually in the range of not more than −10° C. and preferably not more than −15° C.

When a melting point (Tm, ° C.) exists in an endothermic curve of a differential scanning calorimeter (DSC), (ii) the propylene/ethylene/α-olefin random copolymer has the heat of fusion ΔH of not more than 30 J/g and satisfies the following inequality in a relationship between the propylene content ($C_3$ content (mole %)) and the heat of fusion ΔH (J/g). Such a copolymer can be preferably used.

$$\Delta H < 345 Ln(C_3 \text{ content (mole \%)}) - 1492$$

In this case, however, the propylene content is in the range of $76 \leq C_3$ content (mole %)$\leq 90$.

Further, the molecular weight distribution (Mw/Mn, polystyrene standard, Mw: weight average molecular weight, Mn: number average molecular weight) measured by GPC is not more than 4.0, preferably not more than 3.0 and further preferably not more than 2.5.

A part of (ii) the above propylene/ethylene/α-olefin copolymer may be modified, for example, by a graft modification by means of a polar monomer in the ranges in which the object of the present invention is not damaged. Also, other monomers, dienes or the like may be copolymerized in the ranges in which the object is not damaged.

Production of (ii) the propylene/ethylene/α-olefin Random Copolymer

A catalyst to be used for producing (ii) the propylene/ethylene/α-olefin random copolymer used in the present invention is not particularly limited, and it can be prepared by using a catalyst called a Ziegler Natta catalyst, a metallocene catalyst or a post-metallocene catalyst known in the art. In particular, in the present invention, it is preferable to use a metallocene catalyst or a post-metallocene catalyst which is highly copolymerizable.

α-olefin constituting (ii) the propylene/ethylene/α-olefin random copolymer of the present invention is α-olefin having 4 to 20 carbon atoms. Examples of the α-olefin having 4 to 20 carbon atoms include 1-butene, 1-pentene, 1-hexene, 4-methyl-1-pentene, 3-methyl-1-pentene, 1-octene, 3-methyl-1-butene, 1-decene, 1-dodecene, 1-tetradodecene, 1-hexadecene, 1-octadecene, 1-eicosene and the like.

Propylene Based Resin Composition

The propylene based resin composition to be used for the production of the nonwoven fabric of the present invention contains (ii) the propylene/ethylene/α-olefin copolymer in the amount of from 60 to 99 weight parts, based on 1 to 40 weight of (i) the aforementioned isotactic polypropylene. In the present invention, (ii) the propylene/ethylene/α-olefin copolymer is demanded to be contained preferably in the amount of from 70 to 99 weight parts, based on 1 to 30 weight of (i) the isotactic polypropylene. Further, in the present invention, the propylene/ethylene/α-olefin copolymer (ii) is demanded to be contained more preferably in the amount of from 75 to 99 weight parts, based on 1 to 25 weight of (i) the isotactic polypropylene. Incidentally, the total amount of (i) the isotactic polypropylene and (ii) the propylene/ethylene/α-olefin copolymer is 100 weight parts.

As for the aforementioned propylene based resin composition, in an endothermic curve measured by a differential scanning calorimeter (DSC) to the propylene based resin composition, the maximum peak of the melting point (Tm, °C.) exists in the region of not less than 100° C. and the heat of fusion in the maximum peak is in the range of from 5 to 40 J/g.

Furthermore, in the propylene based resin composition used in the present invention, a melt flow rate (ASTM D 1238, at 230° C. under a load of 2.16 kg) is usually from 0.1 to 2000 g/10 minutes, preferably not less than 0.1 g/10 minutes but less than 250 g/10 minutes, and further preferably from 0.1 to 100 g/10 minutes.

Production of the Propylene Based Resin Composition

To produce the nonwoven fabric of the present invention, it is preferable that (i) the isotactic polypropylene and (ii) the propylene/ethylene/α-olefin copolymer are previously kneaded to produce a propylene based resin composition, and then this propylene based resin composition is used for spinning to form a nonwoven fabric. Here, the propylene based resin composition can be produced by employing a method comprising mixing each component in the above range in accordance with various known methods such as a multistage polymerization method, a Henschel mixer, a V-blender, a ribbon blender, a tumbler blender or the like, or a method comprising mixing each component and thereafter melt-kneading by a single screw extruder, a twin screw extruder, a kneader, a Bunbury mixer or the like, followed by granulating or pulverizing. For the purpose of securing the moldability according to the production method of the nonwoven fabric, organic peroxide or the like may be added as a degradation accelerator (degradation agent) as needed. Further, the flowability may be obtained according to the production method of the nonwoven fabric to be selected by the reaction of a degradation accelerator (degradation agent) which is added while mixing.

An additives such as a weather resistant stabilizer, a heat resistant stabilizer, an anti-static agent, an anti-slipping agent, an anti-blocking agent, an anti-fogging agent, a lubricant, a pigment, a dye, a plasticizer, an anti-aging agent, a hydrochloric acid absorbent, an antioxidant, a hydrophilizing agent and the like may be blended in the propylene resin composition of the present invention as needed in the ranges in which the object of the present invention is not damaged. Furthermore, other polymers or the like can also be blended in the ranges in which the object of the present invention is not damaged, as far as the meaning of the present invention is not deviated.

Method for Producing a Nonwoven Fabric Comprising the Propylene Based Resin Composition Examples of the method for producing a nonwoven fabric from the propylene based resin composition produced as described above include a staple fiber dry method, a staple fiber wet method, a melt blown method, a spun bonded method, a flush method, a spun laced method (Latest Spinning Technology, p. 117, compiled by The society of Fiber Science and Technology, Japan, published by Koubunshi-kankoukai, 1992) and the like. To produce nonwoven fabrics using the above methods, it is preferable to adjust the melt flow rate of the propylene resin composition in use corresponding to a method to be employed. For example, in the spun bonded method, a melt flow rate measured at 230° C. is preferably in the range of 1 to 200 g/minute and particularly preferably in the range of 10 to 100 g/minute, while in the melt blown method, it is preferably not less than 10 g/minute and particularly preferably in the range of 20 to 1000 g/minute.

In the nonwoven fabric of the present invention comprising the thus-spun web as described above, a diameter of a fiber constituting the nonwoven fabric is generally from about 0.1 to 100 μm. In the nonwoven fabric of the present invention, a relatively fine fiber (for example, not more than 10 μm) and a relatively thick fiber (for example, thicker than 10 μm) may be mixed or laminated. The length of the fiber forming the nonwoven fabric of the present invention is not particularly limited. In the spun bonded method, a continuous fiber is usually used, while in the melt blown method, a continuous fiber or a partially non-continuous fiber is used. In the dry method, a fiber usually having about 1 to several tens of centimeters is generally used.

By forming entanglement in the thus-formed fiber as described above, such a fiber can be formed into a nonwoven fabric. Examples of the method for forming such entanglement include an entangling treatment by means of needle punching, water jetting, ultrasonic sealing and the like or a thermal bonding treatment using a hot embossing roll. Particularly, in the present invention, a method for forming entanglement by the thermal bonding treatment using a hot embossing roll is preferred. In case of the thermal bonding treatment using a hot embossing roll, embossed area percentage of the embossing roll is properly determined, but it is usually from 5 to 30%.

Since the nonwoven fabric of the present invention obtained as described above has good stretch properties, the residual strain remained in the nonwoven fabric is less than 50% after stretching at a stretch ratio of 150% of the nonwoven fabric of the present invention. In particular, in the present invention, the residual strain is preferably not more than 40% and particularly preferably not more than 30%.

By setting the upper limit of the above residual strain in the nonwoven fabric of the present invention to less than 50%, even when the stretchable nonwoven fabric of the present invention is used in clothing materials, sanitary materials and sports materials, it is possible to make collapse of the product shape and the like unnoticeable.

The nonwoven fabric of the present invention usually has a rate of stress maintenance of not less than 30%. This rate of stress maintenance is preferably not less than 35% and particularly preferably not less than 40%. By having the above rate of stress maintenance of not less than 30%, the nonwoven fabric of the present invention is able to have excellent stretch properties. Thus, when the nonwoven fabric of the present invention is used, for example, in clothing materials, sanitary materials and sports materials, it is possible to make collapse of the product shape and the like unnoticeable.

Since the nonwoven fabric of the present invention has high strength, the maximum strength per a basis weight at a width of 25 mm of the nonwoven fabric of the present invention is usually from 0.05 to 1 N/basis weight and preferably from 0.1 to 1 N/basis weight. By having the above maximum strength of not less than 0.05 N/basis weight, the nonwoven fabric of the present invention is able to have excellent stretch properties. So, when the nonwoven fabric of the present invention is used, for example, in clothing materials, sanitary materials and sports materials, it is possible to suppress occurrence of breakage and the like upon wearing or during wearing it.

Since the nonwoven fabric of the present invention has high stretch properties as described above, the elongation at ultimate is usually not less than 150%, preferably not less than 200% and further preferably not less than 250%. By having the above elongation at ultimate of not less than 150%, even when the nonwoven fabric of the present invention is used for the applications requiring stretch properties such as clothing materials, sanitary materials and sports materials, it is possible to suppress occurrence of breakage upon wearing or during wearing it.

The basis weight of the nonwoven fabric of the present invention is not particularly limited as far as it is a basis weight at which a polyolefin is formed into a nonwoven fabric. The basis weight is usually from 1 to 200 g/m².

Furthermore, the nonwoven fabric of the present invention may be a mixture of a fiber obtained by producing a propylene based resin composition from (i) the aforementioned isotactic polypropylene and (ii) the propylene/ethylene/α-olefin copolymer and spinning, and a fiber comprising other resins (hereinafter referred to as a nonwoven fabric comprising a mixed fiber) in the ranges in which the object of the present invention is achieved.

Other resins mentioned herein refer to those usually containing polyolefin as a main component from its purpose. Examples thereof include polyolefins such as a homopolypropylene, a propylene random copolymer containing ethylene of not more than 10 weight % (or a propylene/ethylene random copolymer), linear low density polyethylene, high density polyethylene and the like; and a mixture of polyolefins such as a mixture of a homopolyethylene and high density polyethylene. In particular, when a homopolypropylene or a propylene random copolymer containing ethylene of not more than 10 weight % (or a propylene/ethylene random copolymer) is a main component, a nonwoven fabric which is further excellent in stretch properties and sense of touch can be obtained. These resins may be,
as needed, blended with other resins than the polyolefin based resins; additives such as a weather resistant stabilizer, a heat resistant stabilizer, an anti-static agent, an anti-slipping agent, an anti-blocking agent, an anti-fogging agent, a lubricant, a pigment, a dye, a plasticizer, an anti-aging agent, a hydrochloric acid absorbent, an antioxidant, a hydrophilizing agent and the like in the ranges in which the object of the present invention is not damaged.

As a method for producing the nonwoven fabric comprising this mixed fiber, conventionally known methods can be applied as described, for example, in Japanese Patent Laid-open No. 2002-242069. In this case, the mixture ratio of the fiber comprising other resins is usually not more than 70 weight %, preferably not more than 50 weight % and further preferably not more than 30 weight % of the total nonwoven fabric.

Furthermore, the nonwoven fabric of the present invention may be laminated with other nonwoven fabrics, films or the like in the ranges in which the object of the present invention is not damaged.

The laminate according to the present invention is a laminate containing at least one layer comprising the above stretchable nonwoven fabric. This laminate can be prepared according to the following method. A fiber is deposited in the same manner as described above, and then on this deposit was laminated, for example, a nonwoven fabric having elongatability. Then, the resulting material is fusion bonded. A method of fusion bonding is not particularly limited, but examples thereof include an entangling treatment, a thermal bonding treatment and adhesion using an adhesive as described above. Of the methods, a hot embossing process is preferably used. In case of adhesion using an adhesive, examples of the adhesive include resin based adhesives such as vinyl acetate based adhesives, vinyl chloride based adhesives, polyvinyl alcohol based adhesives and the like; and rubber based adhesives such as styrene-butadiene based adhesives, styrene-isoprene based adhesives, urethane based adhesives and the like. Further, solvent based adhesives obtained by dissolving these adhesives in an organic solvent and emulsified aqueous emulsion adhesives and the like can be mentioned. Of these adhesives, the rubber based hot melt adhesives such as styrene-isoprene, styrene-butadiene and the like are preferably used in that these adhesives do not impair good sense of touch.

The nonwoven fabric having elongatability is not particularly limited as far as it follows the elongation at ultimate of the above stretchable nonwoven fabric. For example, when the laminate is used for sanitary materials of a disposable diaper and the like, a nonwoven fabric comprising a polymer containing polyolefins, particularly polyethylene and/or polypropylene, is preferably used since excellent sense of touch, high stretch properties and excellent heat sealing properties are required. Furthermore, when a hot embossing process is carried out to form the above laminate, as the above elongatability nonwoven fabric, a nonwoven fabric comprising a polymer exhibiting good compatibility with and adhesiveness to the stretchable nonwoven fabric according to the present invention is preferred.

As the fiber forming the stretchable nonwoven fabric, for example, various types of fibers such as mono-component type, core-in-sheath type, splittable conjugate type, island-in-sea type and side-by-side type are preferred and mixed fibers thereof may be used.

Meanwhile, as the laminate according to the present invention, a laminate with a thermoplastic polymer film laminated on a layer comprising the above stretchable nonwoven fabric can be mentioned. The thermoplastic polymer film may be a breathable film or a hole film.

The thus-obtained laminate does not generate peeling between layers since the stretchable nonwoven fabric layer comprising the propylene based polymer composition has excellent heat sealing properties. Further, the laminate is a stretchable laminate which is highly excellent in sense of touch.

Other fiber layers to be laminated in this case are contained usually in the amount of not more than 70 weight %, preferably not more than 50 weight % and further preferably not more than 30 weight % of the total basis weight of the nonwoven fabric. Further, the laminate may be subjected to a process such as a stretching process or the like in the ranges in which the present invention is not damaged. As the stretching processing method, conventionally known methods can be applied. A method of partial stretching or a method of entire stretching may be adopted. Further, uniaxial stretching or biaxial stretching may also be adopted.

The nonwoven fabric of the present invention can be used as various sanitary materials, disposable diapers, sanitary products, absorbent articles, disposable face masks, adhesive plasters, patches, disposable surgeon gowns, rescue gowns and the like, various medical films or sheets, medical gowns, surgery caps, disposable caps and the like since it is highly stretchable.

The concrete applications of the nonwoven fabric of the present invention will be hereinafter described in detail with reference to examples.

Absorbent Articles

Absorbent articles of a disposable diaper, a sanitary product and the like are required to be fitted into the body. Since the nonwoven fabric of the present invention has excellent stretch properties, more specifically, it can be properly used by using these stretch properties in such portions as a top sheet, a back sheet, a waist band (extension tape, side flap), a fastening tape, a three dimensional gather, a leg cuff, a side panel of a pants-type disposable diaper or the like in an unfolding disposable diaper or a pants-type disposable diaper. By using the product of the present invention to these portions, the absorbent articles can follow the movement of wearers, namely, they can be fitted into their respective bodies.

Disposable Face Masks

Disposable face masks generally comprise a covered part near a mouth and an ear loop part extended from both sides of the covered part. To wear a face mask, it is necessary to extend an ear loop part once to hang on the ear so that stretch properties are required. Further, movement of the body is required to be followed. The nonwoven fabric of the present invention is provided with stretch properties so that it can be used in an ear loop part of a disposable face mask, which satisfies these requirements.

Adhesive Plasters and Patches

Sufficient air permeability in order not to cause skin irritations, softness in order not to give a feeling of stiffness, sufficient fitness to the skin have been demanded for a base material to be used in an adhesive plaster and the like. The nonwoven fabric of the present invention has stretch properties and at the same time air permeability, and further excellent stretch properties so that it is suitably used as a base material for these adhesive plasters and the like.

Disposable Surgeon Gowns, Rescue Gowns

Movable joint portions such as an arm, an elbow, a shoulder, a sleeve and the like of a disposable surgeon gown, a rescue gown and the like are required to have air permeability and stretch properties. The nonwoven fabric of the present invention is a nonwoven fabric like a usual nonwoven fabric so that it has air permeability and further excellent stretch properties. So, it is suitably used as a base material to be used for movable joint portions such as an arm, an elbow, a shoulder and the like of these disposable surgeon gowns, rescue gowns and the like.

Meanwhile, since the product of present invention comprises a polypropylene composition, it exhibits excellent effect in adhesiveness to a polyolefin member to be mainly used for disposable applications. That is, if the nonwoven fabric of the present invention is used as described above, it is possible to adhere it to junction portions, for example, by using a hot melt type adhesive or the like. Examples of the hot melt type adhesive include a polyolefin based hot melt adhesive, acrylic type hot melt type adhesive and the like, and the nonwoven fabric of the present invention exhibits excellent affinity for these hot melt type adhesives, thus enabling sure adhesion.

The nonwoven fabric of the present invention is a polypropylene based nonwoven fabric which is excellent in stretch properties and exhibits a small residual strain, and it can be used for various applications as a nonwoven fabric including sanity materials.

In particular, diapers including the nonwoven fabric of the invention achieve superior performance because the nonwoven fabric has excellent elongation and stretch properties and small residual strain, permitting the diaper to be easily attached and maintained and to follow the movements of body. Moreover, the nonwoven fabric naturally provides good air permeability.

EXAMPLES

The present invention is now more specifically illustrated below with reference to Examples. However, the present invention is not restricted to these Examples and the like.

The physical properties, test conditions and the like will be described below.

Evaluation of a polypropylene Composition

[Melting Point (Tm) and Glass Transition Temperature (Tg)]

An endothermic curve of DSC was obtained and a temperature at the maximum peak position was taken as Tm. Tm was obtained from the endothermic curve measured by filling a sample in an aluminum pan, heating to 200° C. at a rate of 100° C./minute, maintaining at 200° C. for 10 minutes, and then cooling down to −150° C. at a rate of 100° C./minute, and then elevating temperature at a rate of 10° C./minute.

[Intrinsic Viscosity [η]]

The intrinsic viscosity was measured in decalin at 135° C.

[Mw/Mn]

Using GPC (gel permeation chromatography), Mw/Mn was measured at 140° C. with an ortho-dichlorobenzene solvent.

Evaluation of a Nonwoven Fabric

[Tensile Test]

Elongation at Ultimate of a Nonwoven Fabric;

5 sheets of sample pieces were cut in a size of 5.0 cm in a machine direction (MD) and 2.5 cm in a cross-machine direction (CD) from the obtained nonwoven fabric. This sample piece was stretched under conditions of a distance between chucks of 30 mm and a tensile rate of 30 mm/minute at a jig of a tensile tester (MODEL 201N type, a product of Intesco Inc.) and the elongation (unit: %) at the maximum load was obtained.

Residual Strain of a Nonwoven Fabric after Stretching at a Stretch Rate of 150%;

5 sheets of sample pieces were cut in a size of 5.0 cm in a machine direction (MD) and 2.5 cm in a cross-machine direction (CD) from the obtained nonwoven fabric. This sample piece was stretched under conditions of a distance between chucks of 30 mm, a tensile rate of 30 mm/minute and a stretch ratio of 150% at a jig of a tensile tester (MODEL 201N type, a product of Intesco Inc.) and then immediately recovered to the original length at the same rate. A strain was measured at a time when the tensile load became zero N. An average of strains was evaluated as a residual strain (unit: %).

Moldability

Easiness in spinning in the production of the nonwoven fabric shown below was evaluated according to the following criteria.

Evaluation of Spinning Moldability

Spinning state near a nozzle surface was visually observed and frequency of filament breakage was counted for 5 minutes (unit: No./5 minutes). Here, [filament breakage] refers to a phenomenon of one filament solely broken during molding, a case where filaments are fusion bonded each other, causing breakage of filaments and the like.

Preparation of a Catalyst

The catalyst used in Synthesis Examples of the present invention was prepared in the following manner.

Upon initiation of polymerization, 0.38 ml of a toluene solution of triphenylcarbenium(tetrakispentafluorophenyl)borate and 0.38 ml of a toluene solution of [dimethyl(t-butylamide)(tetramethyl-$\eta^5$-cyclopentadienyl)silane]titanium dichloride were employed, and 4.24 ml of toluene for diluting was further added thereto. 5 ml of the toluene solution was prepared such that triphenylcarbenium(tetrakispentafluorophenyl)borate became 0.002 mmole/liter in terms of B and [dimethyl(t-butylamide)(tetramethyl-$\eta^5$-cyclopentadienyl)silane]titanium dichloride became 0.0005 mmole/liter in terms of Ti to give a catalyst solution.

Synthesis of a Resin in Use

SYNTHESIS EXAMPLE 1

(Synthesis of a propylene/ethylene/butene Copolymer, PEB-1)

Into a 2000 ml polymerization apparatus sufficiently purged with nitrogen were introduced 833 ml of dry hexane, 100 g of 1-butene and triisobutylaluminum (1.0 mmole) at room temperature, and then the internal temperature of the polymerization apparatus was elevated to 40° C. Propylene was introduced for pressurizing the system such that the pressure inside the system became 0.76 MPa, and then ethylene was introduced for adjusting the pressure inside the system to be 0.8 MPa.

Then, a toluene solution containing 0.001 mmole of dimethylmethylene(3-tert-butyl-5-methylcyclopentadienyl)fluorenyl zirconium dichloride and methylaluminoxane (a product of Tosoh Finechem Corporation) of 0.3 mmole in terms of aluminum were added to the polymerization apparatus. The resultant mixture was polymerized for 20 minutes while maintaining the internal temperature of 40° C. and the pressure inside the system of 0.8 MPa by introducing ethylene and polymerization was stopped by adding 20 ml of methanol. After the pressure was removed, a polymer was precipitated from the polymerization solution in 2 liter of methanol and dried in vacuum at 130° C. for 12 hours. The obtained polymer was 36.4 g and had an intrinsic viscosity [η] of 1.81 dl/g, a glass transition temperature Tg of −29° C., a propylene content of 76 mole %, an ethylene content of 17 mole %, a butene content of 8 mole %, and a molecular weight distribution (Mw/Mn) measured by GPC of 2.1. Further, the clear melting peak could not be confirmed from the heat of fusion measured by DSC.

The propylene/ethylene/1-butene copolymer obtained as described above is taken as PEB-1.

Synthesis Examples 2 TO 7

The partial pressure of each monomer was regulated in the same manner as in Synthesis Example 1 to change the content of the constituent monomer to obtain a propylene based resin composition (Table 1) (PEB-2, PEB-3, PEB-4, PE-5, PEB-6).

TABLE 1

| | Propylene content (mole %) | Ethylene content (mole %) | 1-butene content (mole %) | Intrinsic viscosity dl/g | MFR (g/10 minutes) |
|---|---|---|---|---|---|
| PEB-1 | 75.0 | 17.0 | 8.0 | 1.81 | 8 |
| PEB-2 | 68.0 | 13.0 | 19.0 | 1.88 | 7 |
| PEB-3 | 45.0 | 25.0 | 30.0 | 1.66 | 14 |
| PEB-4 | 65.0 | 10.0 | 25.0 | 1.72 | 10 |
| PE-5 | 80.0 | 20.0 | — | 2.04 | 2 |
| PEB-6 | 70.0 | 5.0 | 25.0 | 1.75 | 9 |

Synthesis Example 8

Synthesis of an ethylene/1-butene Copolymer, EB-9

An ethylene/1-butene copolymer (EB-9) was prepared according to the following method.

<Regulation of a Catalyst Solution>

18.4 mg of triphenylcarbenium(tetrakispentafluorophenyl)borate was employed and 5 ml of toluene was added thereto for dissolving the mixture and regulating a toluene solution with a concentration of 0.004 mmole/ml. Further, 1.8 mg of [dimethyl(t-butylamide)(tetramethyl-$\eta^5$-cyclopentadienyl)silane]titanium dichloride was employed and 5 ml of toluene was added thereto for dissolving the mixture and regulating a toluene solution with a concentration of 0.001 mmole/ml.

Upon initiation of polymerization, 0.38 ml of a toluene solution of triphenylcarbenium(tetrakispentafluorophenyl)borate and 0.38 ml of a toluene solution of [dimethyl(t-butylamide)(tetramethyl-$\eta^5$-cyclopentadienyl)silane]titanium dichloride were employed, and 4.24 ml of toluene for diluting was further added thereto. 5 ml of the toluene solution was regulated such that triphenylcarbenium (tetrakispentafluorophenyl)borate became 0.002 mmole/liter in terms of B and [dimethyl(t-butylamide)(tetramethyl-$\eta^5$-cyclopentadienyl)silane]titanium dichloride became 0.0005 mmole/liter in terms of Ti to give a catalyst solution.

<Polymerization>

Into a 1.5 liter SUS autoclave sufficiently purged with nitrogen, equipped with a stirring blade, was introduced 750 ml of heptane at 23° C.

Into this autoclave, 6 g of 1-butene and 150 ml of hydrogen were introduced while rotating the stirring blade and ice-cooling.

Then, the autoclave was heated up to 100° C. and pressurized with ethylene such that the total pressure became 6 kg/cm².

When the internal pressure of the autoclave became 6 kg/cm², 1.0 ml of a solution obtained by adding hexane to 1.0 mmole/ml of triisobutylaluminum (TIBA) was pressure-fitted with nitrogen. Subsequently, 5 ml of the toluene solution of the above catalyst was press-fitted into the autoclave with nitrogen to initiate polymerization.

Thereafter, the temperature was regulated for 5 minutes such that the internal temperature of the autoclave became 100° C. and ethylene was directly supplied such that the pressure became 6 kg/cm². After 5 minutes since the initiation of polymerization, 5 ml of methanol was put into the autoclave by using a pump to stop polymerization and the autoclave was depressurized to atmospheric pressure. 3 liter of methanol was introduced into the reaction solution while stirring. The obtained polymer containing solvent was dried at 130° C. in 600 Torr for 13 hours to obtain an ethylene/1-butene copolymer (EB-9). Properties of this copolymer (EB-9) are shown in the following Table 2.

The composition ratio (ethylene/1-butene) of the obtained ethylene/1-butene copolymer (EB-9) was 85 mole %/15 mole %.

TABLE 2

Polymer properties of ethylene/1-butene copolymer (EB-9)

| | |
|---|---|
| Density (g/cm³) | 0.893 |
| MFR2 (g/10 minutes) | 70 |
| Mw/Mn | 2.0 |
| MER10/MFR2 | 7.5 |
| Tαβ/Tαα | 0.3 |
| B value | 1.0 |

(1) The density shown in the above Table 2 was obtained at 23° C. in accordance with ASTM D1505. Further, as for (2) MFR, MFR2 was measured at 190° C. under a load of 2.16 kg, while MFR10 was measured at 190° C. under a load of 10 kg, in accordance with ASTM D1238.

Furthermore, (3) the molecular weight distribution (Mw/Mn) was measured under the above conditions according to the gel permeation chromatography.

Incidentally, in the formation of the nonwoven fabric shown in Examples and Comparative Examples, synthesis was carried out at a scale of 100 times or more those in the above Synthesis Examples.

In addition to the above, an isotactic polypropylene (Polypropylene B101, a product of Mitsui Chemicals, inc., MFR: 0.5 g/10 minutes, Tm: 165° C.) was prepared. This polypropylene is taken as iPP-1.

A propylene homopolymer (MFR measured at a temperature of 230° C. under a load of 2.16 kg in accordance with ASTM D1238: 35 g/10 minutes, density: 0.91 g/cm³, Tm: 161° C.) was prepared. This propylene homopolymer is taken as iPP-2.

Synthesis of a syndiotactic polypropylene sPP-1

In accordance with a method as described in Japanese Patent Laid-open No. 1990-274763, a syndiotactic polypropylene was obtained by using a catalyst comprising diphenylmethylene(cyclopentadienyl)fluorenyl zirconium dichloride and methyl aluminoxane in the presence of hydrogen according to a bulk polymerization method of propylene. Its melt flow index was 4.4 g/10 minutes, the molecular weight distribution according to GPC was 2.3, a syndiotactic pentad fraction (r.r.r.r) measured according to $^{13}$C-NMR was 0.823, Tm measured according to a differential scanning calorimetry was 127° C., and Tc was 57° C. This syndiotactic polypropylene is taken as sPP-1.

A polyethylene and propylene based copolymer composition (Z104S) manufactured by Basell Polyolefins Company was prepared. This copolymer composition is taken as EP-8.

Example 1

5 weight % of Mitsui polypropylene (B101: MFR: 0.5, Tm: 165° C., iPP-1), 95 weight % of the propylene/ethylene/1-butene copolymer (PEB-2, propylene content: 68 mole %, ethylene content: 13 mole %, 1-butene content: 19.0 mole %, MFR: 8 g/10 minutes) obtained in Synthesis Example 2, a degradation agent (product name: PH25B, a product of Nippon Oils and Fats Co., Ltd.) of 0.02 weight % based on the total weight of iPP-1 and PEB-2 were mixed. The resulting mixture was kneaded at 200° C. using a twin screw extruder to prepare a propylene polymer composition (composition 1). An endothermic curve to this composition 1 was measured using a differential scanning calorimeter (DSC). As a result, the maximum peak of the melting point (Tm, ° C.) was 154.2° C., while the heat of fusion in this maximum peak was 5 J/g.

The thus-obtained propylene based polymer composition 1 was spun under the conditions of a die temperature of 290° C. and a single hole discharge rate of 1 g/minute/hole using a molding machine for spunbonding having a spinning nozzle with a nozzle diameter of 0.6 mmφ and a nozzle pitch of 8 mm lengthwise and 9 mm breadthwise, and stretched under the conditions of a cooling air temperature of 20° C. and stretching air rate of 2000 m/minute to deposit a web comprising the above composition 1 on a collection area.

The deposited web was subjected to an embossing process (embossed area percentage: 7%, embossing roll diameter: 150 mmφ, marking pitch: 2.1 mm lengthwise and breadthwise, marking shape: rhombus) at 70° C. to prepare a spunbonded nonwoven fabric having a basis weight of 100 g/m².

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 21% after stretching at a stretch ratio of 150%, is good at sense of touch, has an elongation at ultimate of 423% which is in the practical range, and is also excellent in spinnability.

Example 2

A propylene polymer composition (composition 2) was prepared in the same manner as in Example 1, except that the amount of polypropylene iPP-1 used was changed to 40 weight % and the amount of the propylene/ethylene/1-butene copolymer PEB-2 used was changed to 60 weight %. An endothermic curve to this composition 2 was measured using a differential scanning calorimeter (DSC). As a result, the maximum peak of the melting point (Tm, ° C.) was 155.5° C., while the heat of fusion in this maximum peak was 40 J/g.

Furthermore, a spunbonded nonwoven fabric having a basis weight of 100 g/m² was prepared in the same manner as in Example 1, except that this propylene polymer composition (composition 2) was used.

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 37% after stretching at a stretch ratio of 150%, is good at sense of touch, has an elongation at ultimate of 373% which is in the practical range, and is also excellent in spinnability.

Example 3

A propylene polymer composition (composition 3) was prepared in the same manner as in Example 1, except that the amount of polypropylene iPP-1 used was changed to 15 weight % and the amount of the propylene/ethylene/1-butene copolymer PEB-2 used was changed to 85 weight %. An endothermic curve to this composition 3 was measured using a differential scanning calorimeter (DSC). As a result, the maximum peak of the melting point (Tm, °C.) was 154.6° C., while the heat of fusion in this maximum peak was 15 J/g.

Furthermore, a spunbonded nonwoven fabric having a basis weight of 100 g/m² was prepared in the same manner as in Example 1, except that this propylene polymer composition (composition 3) was used.

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 29% after stretching at a stretch ratio of 150%, is good at sense of touch, has an elongation at ultimate of 393% which is in the practical range, and is also excellent in spinnability.

Example 4

A propylene polymer composition (composition 3) was prepared in the same manner as in Example 1, except that the amount of polypropylene iPP-1 used was changed to 15 weight % and the amount of the propylene/ethylene/1-butene copolymer PEB-2 used was changed to 85 weight %.

Furthermore, a spunbonded nonwoven fabric having a basis weight of 100 g/m² was prepared in the same manner as in Example 1, except that this propylene polymer composition (composition 3) was used and a single hole discharge rate was 0.6 g/minute·hole.

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 30% after stretching at a stretch ratio of 150%, is good at sense of touch, has an elongation at ultimate of 409% which is in the practical range, and is also excellent in spinnability.

Example 5

A propylene polymer composition (composition 3) was prepared in the same manner as in Example 1, except that the amount of polypropylene iPP-1 used was changed to 15 weight % and the amount of the propylene/ethylene/1-butene copolymer PEB-2 used was changed to 85 weight %.

Furthermore, a spunbonded nonwoven fabric was prepared in the same manner as in Example 1, except that this propylene polymer composition (composition 3) was used and a basis weight was 50 g/m².

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 30% after stretching at a stretch ratio of 150%, is good at sense of touch, has an elongation at ultimate of 260% which is in the practical range, and is also excellent in spinnability.

Example 6

A propylene polymer composition (composition 4) was prepared in the same manner as in Example 1, except that the amount of polypropylene iPP-1 used was changed to 10 weight % and 90 weight % of the propylene/ethylene/1-butene copolymer (PEB-3, propylene content: 45.0 mole %, ethylene content: 25.0 mole %, 1-butene content: 30.0 mole %) obtained in Synthesis Example 3 was used instead of the propylene/ethylene/1-butene copolymer PEB-2. An endothermic curve to this composition 4 was measured using a differential scanning calorimeter (DSC). As a result, the maximum peak of the melting point (Tm, °C.) was 154.2° C., while the heat of fusion in this maximum peak was 10 J/g.

Furthermore, a spunbonded nonwoven fabric having a basis weight of 100 g/m² was prepared in the same manner as in Example 1, except that this propylene polymer composition (composition 4) was used.

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 40% after stretching at a stretch ratio of 150%, is good at sense of touch, has an elongation at ultimate of 410% which is in the practical range, and is also excellent in spinnability.

Example 7

A propylene polymer composition (composition 5) was prepared in the same manner as in Example 1, except that the amount of polypropylene iPP-1 used was changed to 10 weight % and 90 weight % of the propylene/ethylene/1-butene copolymer (PEB-4, propylene content: 65.0 mole %, ethylene content: 10.0 mole %, 1-butene content: 25.0 mole %) obtained in Synthesis Example 4 was used instead of the propylene/ethylene/1-butene copolymer PEB-2. An endothermic curve to this composition 5 was measured using a differential scanning calorimeter (DSC). As a result, the maximum peak of the melting point (Tm, °C.) was 153.1° C., while the heat of fusion in this maximum peak was 10 J/g.

Furthermore, a spunbonded nonwoven fabric having a basis weight was 100 g/m² was prepared in the same manner as in Example 1, except that this propylene polymer composition (composition 5) was used.

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 33% after stretching at a stretch ratio of 150%, is good at sense of touch, has an elongation at ultimate of 413% which is in the practical range, and is also excellent in spinnability.

Example 8

A propylene polymer composition (composition 6) was prepared in the same manner as in Example 1, except that the amount of polypropylene iPP-1 used was changed to 10 weight % and 90 weight % of the propylene/ethylene copolymer (PE-5, propylene content: 80.0 mole %, ethylene content: 20.0 mole %) obtained in Synthesis Example 5 was used instead of the propylene/ethylene/1-butene copolymer PEB-2. An endothermic curve to this composition 6 was measured using a differential scanning calorimeter (DSC). As a result, the maximum peak of the melting point (Tm, °C.) was 153.9° C., while the heat of fusion in this maximum peak was 10 J/g.

Furthermore, a spunbonded nonwoven fabric having a basis weight was 100 g/m² was prepared in the same manner as in Example 1, except that this propylene polymer composition (composition 6) was used.

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 30% after stretching at a stretch ratio of 150%, is good at sense of touch, has an elongation at ultimate of 469% which is in the practical range, and is also excellent in spinnability.

Example 9

20 weight % of Mitsui polypropylene (B101: MFR: 0.5, Tm: 165° C.) (iPP-1) and 80 weight % of the propylene/ethylene/butene copolymer (PEB-1, propylene content: 75.0 mole %, ethylene content: 17.0 mole %, 1-butene content: 8.0 mole %) obtained in Synthesis Example 1 were kneaded at 200° C. using a twin screw extruder to obtain a propylene based polymer composition (composition 7). An endothermic curve to this composition 7 was measured using a differential scanning calorimeter (DSC). As a result, the maximum peak of the melting point (Tm, ° C.) was 153.4° C., while the heat of fusion in this maximum peak was 10 J/g.

The thus-obtained composition 7 was melt-spun under the conditions of a die temperature of 290° C. and a single hole discharge rate of 1.0 g/(minute hole), a cooling air temperature of 20° C. and stretching air rate of 2000 m/minute using a molding machine for spunbonding having a spinning nozzle with a nozzle diameter of 0.6 mmφ, a nozzle pitch of 8 mm lengthwise and 9 mm breadthwise to deposit a web comprising the composition 7 on a collection area. This web was subjected to an embossing process (embossed area percentage: 7%, embossing roll diameter: 150 mmφ, marking pitch: 2.1 mm lengthwise and breadthwise, marking shape: rhombus) at 70° C. to prepare a spunbonded nonwoven fabric having a basis weight of 165 g/m².

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 22% after stretching at a stretch ratio of 150%, is good at sense of touch, has an elongation at ultimate of 732% which is in the practical range, and is also excellent in spinnability.

Example 10

20 weight % of a propylene homopolymer (iPP-2) having MFR (measured at a temperature of 230° C. under a load of 2.16 kg in accordance with ASTM D1238) of 30 g/10 minutes, a density of 0.91 g/cm³ and a melting point of 160° C., and 80 weight % of the propylene/ethylene/butene copolymer (PEB-1, propylene content: 75.0 mole %, ethylene content: 17.0 mole %, 1-butene content: 8.0 mole %) obtained in Synthesis Example 1 were kneaded at 200° C. using a twin screw extruder to obtain a propylene based polymer composition (composition 8). An endothermic curve to this composition 8 was measured using a differential scanning calorimeter (DSC). As a result, the maximum peak of the melting point (Tm, ° C.) was 153.3° C., while the heat of fusion in this maximum peak was 20 J/g.

The thus-obtained composition 8 was melt-spun under the conditions of a die temperature of 250° C., a single hole discharge rate of 1.0 g/(minute·hole), a cooling air temperature of 20° C. and stretching air rate of 2000 m/minute using a molding machine for spunbonding having a spinning nozzle with a nozzle diameter of 0.6 mmφ, a nozzle pitch of 8 mm lengthwise and 9 mm breadthwise to deposit a web comprising the composition 8 on a collection area. This web was subjected to an embossing process (embossed area percentage: 7%, embossing roll diameter: 150 mmφ, marking pitch: 2.1 mm lengthwise and breadthwise, marking shape: rhombus) at 70° C. to prepare a spunbonded nonwoven fabric having a basis weight of 156 g/m².

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 24% after stretching at a stretch ratio of 150%, is good at sense of touch, has an elongation at ultimate of 452% which is in the practical range, and is also excellent in spinnability.

Comparative Example 1

A propylene polymer composition (composition 9) was prepared in the same manner as in Example 1, except that the amount of polypropylene iPP-1 used was changed to 50 weight % and the amount of the propylene/ethylene/1-butene copolymer PEB-2 used was changed to 50 weight %. An endothermic curve to this composition 9 was measured using a differential scanning calorimeter (DSC). As a result, the maximum peak of the melting point (Tm, ° C.) was 155.8° C., while the heat of fusion in this maximum peak was 50 J/g. Furthermore, a spunbonded nonwoven fabric having a basis weight of 100 g/m² was prepared in the same manner as in Example 1, except that this propylene polymer composition (composition 9) was used.

Compositions of the resin constituting the obtained nonwoven fabric, production conditions of the nonwoven fabric and properties of the nonwoven fabric are shown in Table 3.

As shown in Table 3, the obtained nonwoven fabric has a big residual strain of 58% after stretching at a stretch ratio of 150%, is inferior in stretch properties, is not good at sense of touch, and has a small elongation at ultimate of 150%.

Comparative Example 2

A propylene polymer composition (composition 10) was prepared in the same manner as in Example 1, except that the amount of polypropylene iPP-1 used was changed to 10 weight % and 90 weight % of the propylene/ethylene/1-butene copolymer (PEB-6, propylene content: 70.0 mole %, ethylene content: 5.0 mole %, 1-butene content: 25.0 mole %) obtained in Synthesis Example 6 was used instead of the propylene/ethylene/1-butene copolymer PEB-2. An endothermic curve to this composition 10 was measured using a differential scanning calorimeter (DSC). As a result, the maximum peak of the melting point (Tm, ° C.) was 154.3° C., while the heat of fusion in this maximum peak was 10 J/g.

Furthermore, a spunbonded nonwoven fabric having a basis weight of 100 g/m² was prepared in the same manner as in Example 1, except that this propylene polymer composition (composition 10) was used.

Compositions of the resin constituting the obtained nonwoven fabric, production conditions of the nonwoven fabric and properties of the nonwoven fabric are shown in Table 3.

As shown in Table 3, the obtained nonwoven fabric has a big residual strain of 54% after stretching at a stretch ratio of 150%, and is not good at sense of touch.

Comparative Example 3

A propylene polymer composition (composition 11) was prepared in the same manner as in Example 1, except that 10 weight % of the syndiotactic polypropylene sPP-1 was used instead of polypropylene iPP-1 and 90 weight % of the propylene/ethylene copolymer (PE-5, propylene content: 80.0 mole %, ethylene content: 20.0 mole %) obtained in Synthesis Example 5 instead of the propylene/ethylene/1-butene copolymer PEB-2. An endothermic curve to this composition 11 was measured using a differential scanning calorimeter (DSC). As a result, the maximum peak of the melting point (Tm, ° C.) was 153.2° C., while the heat of fusion in this maximum peak was 10.01 J/g.

Furthermore, a spunbonded nonwoven fabric having a basis weight of 100 g/m² was prepared in the same manner as in Example 1, except that this propylene polymer composition (composition 11) was used.

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 29% after stretching at a stretch ratio of 150%, while filament breakage occurred 15 times for 5 minutes during spinning. Thus, the spinnability is very bad.

Comparative Example 4

An endothermic curve to Z104S manufactured by Basell Polyolefins Company in Example 1 was measured using a differential scanning calorimeter (DSC). As a result, the maximum peak of the melting point (Tm, ° C.) was 141.9° C., while the heat of fusion in this maximum peak was 25 J/g.

Furthermore, a spunbonded nonwoven fabric was prepared in the same manner as in Example 1, except that Z104S manufactured by Basell Polyolefins Company was used, a resin discharge temperature was changed to 240° C., a single hole discharge amount was changed to 0.6 g/minute·hole, a stretching air rate was changed to 4000 m/minute, and a basis weight was changed to 80 g/m².

Compositions of the resin constituting the obtained nonwoven fabric, production conditions of the nonwoven fabric and properties of the nonwoven fabric are shown in Table 3.

As shown in Table 3, the obtained nonwoven fabric has a big residual strain of 67% after stretching at a stretch ratio of 150%, and was not good at sense of touch either.

Comparative Example 5

Without using polypropylene iPP-1 in Example 1, the amount of the ethylene/1-butene copolymer (EB-9, ethylene content: 85 mole %, 1-butene content: 15 mole %) obtained in Synthesis Example 8 was 100 weight %.

Furthermore, a spunbonded nonwoven fabric was prepared in the same manner as in Example 1, except that using the ethylene/1-butene copolymer (EB-9), a resin discharge temperature was changed to 200° C., a single hole discharge amount was changed to 0.6 g/minute·hole, a stretching air rate was changed to 3000 m/minute, and a basis weight was changed to 70 g/m².

Compositions of the resin constituting the obtained nonwoven fabric, production conditions of the nonwoven fabric and properties of the nonwoven fabric are shown in Table 3.

As shown in Table 3, the obtained nonwoven fabric was used for the measurement of a residual strain after stretching at a stretch ratio of 150%, but it was broken so that the residual strain could not be measured. Further, an elongation at ultimate of the nonwoven fabric was 90%.

As shown in Table 3, the obtained nonwoven fabric did not have an effective elasticity since the nonwoven fabric was broken in the measurement test of the residual strain after stretching at a stretch ratio of 150%. Accordingly, this nonwoven fabric was determined as inappropriate for use in an absorbent article such as a disposable diaper and a sanitary material and a disposable face mask, an adhesive plaster, a patch, a disposable surgeon gown, a rescue gown or the like, various medical films, sheets and the like, in which the stretch properties are required.

TABLE 3

| | Composition of fiber constituting nonwoven fabric | | | |
|---|---|---|---|---|
| | Polypropylene and others | | PEBR and others | |
| | Kind | Amount weight % | Kind | Amount weight % |
| Example 1 | iPP-1 | 5 | PEB-2 | 95 |
| Example 2 | iPP-1 | 40 | PEB-2 | 60 |
| Example 3 | iPP-1 | 15 | PEB-2 | 85 |
| Example 4 | iPP-1 | 15 | PEB-2 | 85 |
| Example 5 | iPP-1 | 15 | PEB-2 | 85 |
| Example 6 | iPP-1 | 10 | PEB-3 | 90 |
| Example 7 | iPP-1 | 10 | PEB-4 | 90 |
| Example 8 | iPP-1 | 10 | PE-5 | 90 |
| Example 9 | iPP-1 | 20 | PEB-1 | 80 |
| Example 10 | iPP-2 | 20 | PEB-1 | 80 |
| Comparative Example 1 | iPP-1 | 50 | PEB-2 | 50 |
| Comparative Example 2 | iPP-1 | 10 | PEB-6 | 90 |
| Comparative Example 3 | sPP-1 | 10 | PEB-1 | 90 |
| Comparative Example 4 | EP-8*[1] | | | |
| Comparative Example 5 | — | — | EB-9 | 100 |

| | Production conditions of nonwoven fabric | | | | |
|---|---|---|---|---|---|
| | Production method of nonwoven fabric | Discharge temperature of resin (° C.) | Single hole Discharge amount g/min·hole | Stretching air rate m/min. | Emboss temperature (° C.) |
| Example 1 | Spun bonding | 230 | 1 | 2000 | 70 |
| Example 2 | Spun bonding | 230 | 1 | 2000 | 70 |
| Example 3 | Spun bonding | 230 | 1 | 2000 | 70 |
| Example 4 | Spun bonding | 230 | 0.6 | 2000 | 70 |
| Example 5 | Spun bonding | 230 | 1 | 2000 | 70 |
| Example 6 | Spun bonding | 230 | 1 | 2000 | 70 |
| Example 7 | Spun bonding | 230 | 1 | 2000 | 70 |
| Example 8 | Spun bonding | 230 | 1 | 2000 | 70 |
| Example 9 | Spun bonding | 290 | 1 | 2000 | 70 |
| Example 10 | Spun bonding | 250 | 1 | 2000 | 70 |
| Comparative Example 1 | Spun bonding | 230 | 1 | 2000 | 70 |
| Comparative Example 2 | Spun bonding | 230 | 1 | 2000 | 70 |
| Comparative Example 3 | Spun bonding | 230 | 1 | 2000 | 70 |
| Comparative Example 4 | Spun bonding | 240 | 0.6 | 4000 | 70 |
| Comparative Example 5 | Spun bonding | 200 | 0.6 | 3000 | 70 |

TABLE 3-continued

| | Characteristics of nonwoven fabric | | | |
|---|---|---|---|---|
| | Basis weight g/m² | Elongation at ultimate (%) | Residual strain after stretching at a stretch rate of 150% | Moldability of nonwoven fabric Frequency of filament breakage No./5 minutes |
| Example 1 | 100 | 423 | 21 | 0 |
| Example 2 | 100 | 373 | 37 | 0 |
| Example 3 | 100 | 393 | 29 | 0 |
| Example 4 | 100 | 409 | 30 | 0 |
| Example 5 | 50 | 260 | 30 | 0 |
| Example 6 | 100 | 410 | 40 | 0 |
| Example 7 | 100 | 413 | 33 | 0 |
| Example 8 | 100 | 469 | 32 | 0 |
| Example 9 | 165 | 732 | 22 | 0 |
| Example 10 | 156 | 452 | 24 | 0 |
| Comparative Example 1 | 100 | 150 | 58 | 0 |
| Comparative Example 2 | 100 | — | 54 | 0 |
| Comparative Example 3 | 100 | — | 29 | 15 |
| Comparative Example 4 | 80 | — | 67 | 0 |
| Comparative Example 5 | 70 | 90 | Broken | 0 |

Note)
*[1]Copolymer composition of polypropylene and propylene based polymer Z104S manufactured by Basell Polyolefins Company (EP-8)

Example 11

A propylene polymer composition (composition 3) was prepared using the polypropylene iPP-1 in an amount of 15 weight % and the propylene/ethylene/1-butene copolymer PEB-2 in an amount of 85 weight %.

Figure 2:
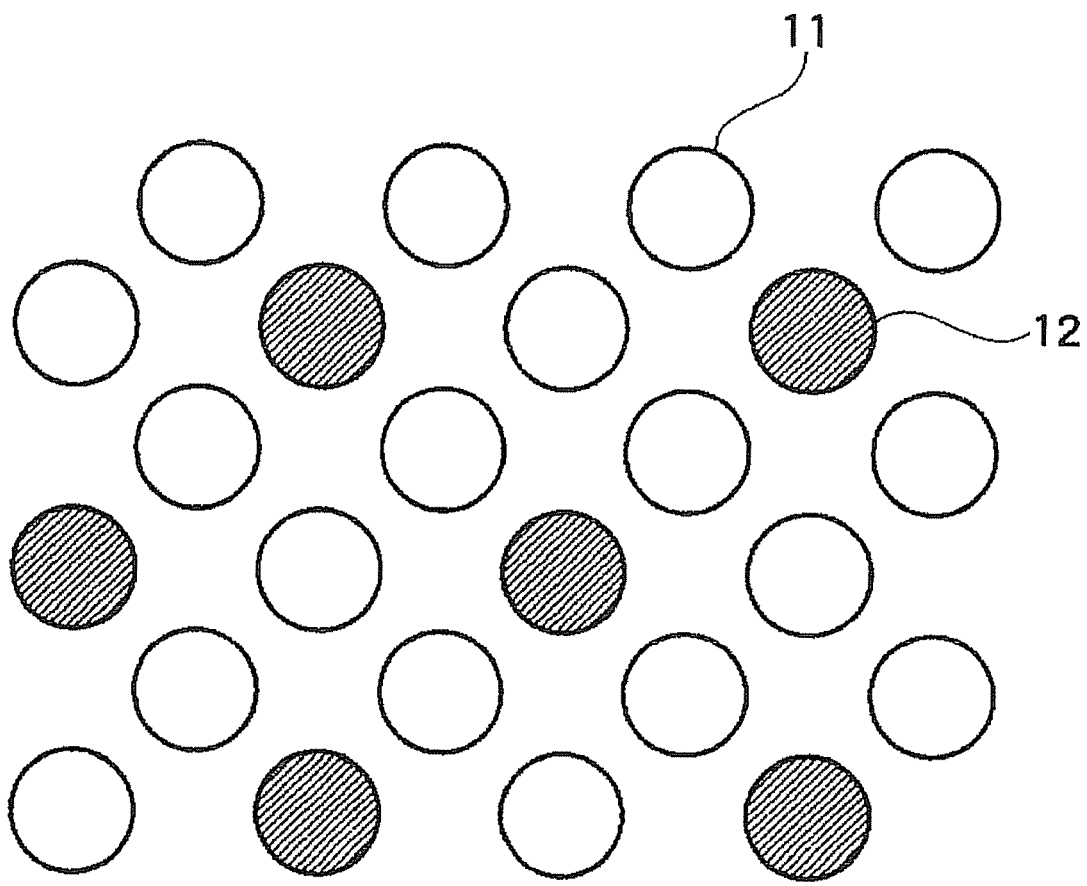
FIG. 2 is a partial view of pattern placement of a nozzle arranged in the nonwoven fabric manufacturing machine as shown in FIG. 1.

A mixture 1 of 92 weight parts of a propylene homopolymer (i-PP-3) having MFR (measured at a temperature of 230° C. under a load of 2.16 kg in accordance with ASTM D1238) of 60 g/10 minutes, a density of 0.91 g/cm³, a melting point of 160° C., and 8 weight parts of a high density polyethylene (hereinafter referred to simply as HDPE) having MFR (measured at a temperature of 190° C. under a load of 2.16 kg in accordance with ASTM D1238) of 5 g/10 minutes, a density 0.97 g/cm³, a melting point of 134° C., and the composition 3 were each independently melted by using an extruder (30 mmφ), and then melt-spun under the conditions of a resin temperature and a die temperature of 230° C., a cooling air temperature of 20° C. and a stretching air rate of 2000 m/minute according to a spunbonding method using a nonwoven fabric manufacturing machine (a molding machine for spunbonding, length of a direction vertical to a machine direction on the collection area: 100 mm) as shown in FIG. 1 having a spinning nozzle as shown in FIG. 2. A web comprising a mixed fiber including a fiber A comprising the mixture 1 and a fiber B comprising the composition 3 was deposited on a collection area such that the weight ratio of the mixture 1 and the composition 3 was adjusted to be 20 weight %:80 weight %.

Namely, in this Example, a nonwoven fabric was prepared by using a nonwoven fabric manufacturing machine which was capable of spinning two different kinds of resins at the same time, as shown in FIG. 1. In the nonwoven fabric manufacturing machine as shown in FIG. 1, a nozzle as shown in FIG. 2 was placed.

Incidentally, in FIG. 1, the number 1 is a first extruder, the number 1' is a second extruder, and resins of different kinds are used in the first extruder and the second extruder. In FIG. 1, the number 2 is a spinning nozzle, the number 3 is a continuous filament, the number 4 is cooling air, the number 5 is an ejector, the number 6 is a capture device, the number 7 is an aspirator, the number 8 is a web, and the number 9 is a take-up roll. In FIG. 2, the number 11 and the number 12 are nozzles for melt-spinning a spunbonded nonwoven fabric, while from the nozzles 11 and 12, resins of different kinds are discharged.

The aforementioned spinning nozzle had a pattern with nozzles arranged therein as shown in FIG. 2 having a nozzle diameter of 0.6 mmφ, a nozzle pitch of 8 mm lengthwise and 9 mm breadthwise, and the ratio of the nozzle number for the fiber A to the nozzle number for the fiber B was 1:3. A single hole discharge amount of the fiber A was 0.45 g/(minute·hole), while a single hole discharge amount of the fiber B was 0.6 g/(minute·hole).

The deposited web was subjected to an embossing process (embossed area percentage: 7%, embossing roll diameter: 150 mmφ, marking pitch: 2.1 mm lengthwise and 2.1 mm breadthwise, marking shape: rhombus) at 70° C. to prepare a spunbonded nonwoven fabric having a basis weight of 50 g/m².

Compositions of the resin constituting the obtained nonwoven fabric, production conditions of the nonwoven fabric and properties of the nonwoven fabric are shown in Table 3.

As shown in Table 3, the obtained nonwoven fabric has a small residual strain of 39% after stretching at a stretch ratio of 150%, is good at sense of touch, has an elongation at ultimate of 340% which is in the practical range, and is also excellent in spinnability.

Example 12

A spunbonded nonwoven fabric having a basis weight of 50 g/m² was prepared in the same manner as in Example 11, except that PE-5 as a resin used for the fiber B was used. An endothermic curve to this composition was measured using a differential scanning calorimeter (DSC). As a result, the maximum peak of the melting point (Tm, ° C.) was 154.0° C., while the heat of fusion in this maximum peak was 31 J/g.

Compositions of the resin constituting the obtained nonwoven fabric, production conditions of the nonwoven fabric and properties of the nonwoven fabric are shown in Table 4.

As shown in Table 4, the obtained nonwoven fabric has a small residual strain of 40% after stretching at a stretch ratio of 150%, is good at sense of touch, has an elongation at ultimate of 352% which is in the practical range, and is also excellent in spinnability.

Example 13

A spunbonded nonwoven fabric having a basis weight of 25 g/m² was prepared in the same manner as in Example 12, except that a basis weight was changed.

Compositions of the resin constituting the obtained nonwoven fabric, production conditions of the nonwoven fabric and properties of the nonwoven fabric are shown in Table 4.

As shown in Table 4, the obtained nonwoven fabric has a small residual strain of 40% after stretching at a stretch ratio of 150%, is good at sense of touch, has an elongation at ultimate of 280% which is in the practical range, and is also excellent in spinnability.

TABLE 4

| | First compositions of fiber constituting nonwoven fabric | | | | Second compositions of fiber constituting nonwoven fabric | | |
|---|---|---|---|---|---|---|---|
| | Polypropylene and others | | PEBR and others | | | | |
| | Kind | Amount weight % | Kind | Amount weight % | B fiber weight ratio | i-PP-3 Amount weight % | HDPE Amount weight % | A fiber weight ratio |
| Example 11 | iPP-1 | 15 | PEB-2 | 85 | 80 | 92 | 8 | 20 |
| Example 12 | iPP-1 | 15 | PE-5 | 85 | 80 | 92 | 8 | 20 |
| Example 13 | iPP-1 | 15 | PE-5 | 85 | 80 | 92 | 8 | 20 |

| | Production conditions of nonwoven fabric | | | | |
|---|---|---|---|---|---|
| | Production method of nonwoven fabric | Discharge temperature of resin (° C.) | Single hole Discharge amount g/min · hole | Stretching air rate m/min. | Emboss temperature (° C.) |
| Example 11 | Mixed fiber Spun bonding | 230 | A0. 45 B0. 60 | 2000 | 70 |
| Example 12 | Mixed fiber Spun bonding | 230 | A0. 45 B0. 60 | 2000 | 70 |
| Example 13 | Mixed fiber Spun bonding | 230 | A0. 45 B0. 60 | 2000 | 70 |

| | Characteristic of nonwoven fabric | | | |
|---|---|---|---|---|
| | Basis weight g/m² | Elongation at ultimate (%) | Residual strain after stretching at a stretch rate of 150% | Moldability of nonwoven fabric Frequency of filament breakage No./5 minutes |
| Example 11 | 50 | 340 | 39 | 0 |
| Example 12 | 50 | 352 | 40 | 0 |
| Example 13 | 25 | 280 | 40 | 0 |

INDUSTRIAL APPLICABILITY

The nonwoven fabric of the present invention is excellent in stretch properties and exhibits a small residual strain after stretching at a stretch ratio of 150%. Accordingly, the nonwoven fabric of the present invention can be used as an absorbent of a sanitary material, a disposable diaper and the like, a ground fabric of an adhesive bandage, a disposable surgeon gown, a rescue gown and the like, which are stretchable during its use.

Furthermore, the nonwoven fabric of the present invention has a great affinity for an adhesive such as an olefin based adhesive or the like, and therefore a junction portion or the like can be joined, for example, by using an olefin based hot melt adhesive or the like.

What is claimed is:

1. A nonwoven fabric obtained by forming a mixture comprising
   (I) a fiber obtained by producing a propylene based resin composition from
   (i) 1 to 40 weight parts of an isotactic polypropylene and
   (ii) 60 to 99 weight parts of a propylene/ethylene/α-olefin copolymer and spinning, and
   (II) a fiber obtained by producing a resin other than the propylene based resin composition and spinning,
   wherein said propylene/ethylene/α-olefin copolymer is obtained by copolymerizing 45 to 89 mole % of propylene, 10 to 25 mole % of ethylene and the balance of α-olefin having 4 to 20 carbon atoms, with the proviso that the copolymerized amount of the α-olefin having 4 to 20 carbon atoms does not exceed 30 mole %.

2. The nonwoven fabric according to claim 1, wherein a residual strain of said nonwoven fabric after stretching at a stretch ratio of 150% is less than 50%.

3. The nonwoven fabric according to claim 1, wherein said nonwoven fabric is a spunbonded nonwoven fabric.

4. The nonwoven fabric according to claim 1, wherein said polypropylene resin composition forming the nonwoven fabric has a maximum peak of a melting point (Tm, ° C.) existing in a region of an endothermic curve of not less than 100° C., determined by a differential scanning calorimeter (DSC), and the heat of fusion in the maximum peak in the range of 5 to 40 J/g.

5. A sanitary material having the nonwoven fabric according to claim 1.

6. A disposable diaper having the nonwoven fabric according to claim 1.

7. A sanitary material having the nonwoven fabric according to claim 1.

8. An absorbent article having the nonwoven fabric according to claim 1.

9. A disposable face mask having the nonwoven fabric according to claim 1.

10. An adhesive plaster having the nonwoven fabric according to claim 1.

11. A patch having the nonwoven fabric according to claim 1.

12. A disposable surgeon gown having the nonwoven fabric according to claim 1.

13. A rescue gown having the nonwoven fabric according to claim 1.

14. Various medical films or sheets having the nonwoven fabric according to claim 1.

15. A sanitary material having the nonwoven fabric according to claim 4.

16. A disposable diaper having the nonwoven fabric according to claim 4.

17. A sanitary material having the nonwoven fabric according to claim 4.

18. An absorbent article having the nonwoven fabric according to claim 4.

19. A disposable face mask having the nonwoven fabric according to claim 4.

20. An adhesive plaster having the nonwoven fabric according to claim 4.

21. A patch having the nonwoven fabric according to claim 4.

22. A disposable surgeon gown having the nonwoven fabric according to claim 4.

23. A rescue gown having the nonwoven fabric according to claim 4.

24. Various medical films or sheets having the nonwoven fabric according to claim 4.

* * * * *